United States Patent [19]

Hutson

[11] Patent Number: 4,494,534
[45] Date of Patent: Jan. 22, 1985

[54] UNIVERSAL LEG BRACE SYSTEM
[75] Inventor: Floyd E. Hutson, Arlington, Tex.
[73] Assignee: Medical Designs, Inc., Azle, Tex.
[21] Appl. No.: 472,927
[22] Filed: Mar. 7, 1983
[51] Int. Cl.³ .............................................. A61F 3/00
[52] U.S. Cl. ..................................... 128/80 F; 128/88
[58] Field of Search ............... 128/80 R, 80 C, 80 F, 128/80 H, 87 R, 88, DIG. 15

[56] References Cited

U.S. PATENT DOCUMENTS 4,320,748  3/1982  Racette et al. ............... 128/80 F
4,407,276  10/1983 Bledsoe ........................ 128/80 C Primary Examiner—John D. Yasko
Attorney, Agent, or Firm—Wofford, Fails & Zobal

[57] ABSTRACT

A universal leg brace system for controlling the degree of motion permitted by a wearer's knee characterized by respective flexible sheets of cushioned material adapted for snugly wrapping around the wearer's thigh and calf; elongate braces that are stiff and adapted to lie on opposite sides of the wearer's thigh connected with a hinge positioned on opposite sides of the wearer's knee; rear stays connected with the respective sheets for providing structural support in the longitudinal direction longitudinally of the posterior of the thigh and calf; tibial and femoral plates connected with the first and second flexible sheets for providing significant structual support in the longitudinal direction along the anterior portion of the tibia and femur; straps and Velcro for adjustably positioning and selectively attaching the respective braces, sheets, plates and the like by circumferentially encompassing the leg of the wearer to provide significant longitudinal support without the requirement for a heavy, relatively permanent cast or the like.

18 Claims, 13 Drawing Figures

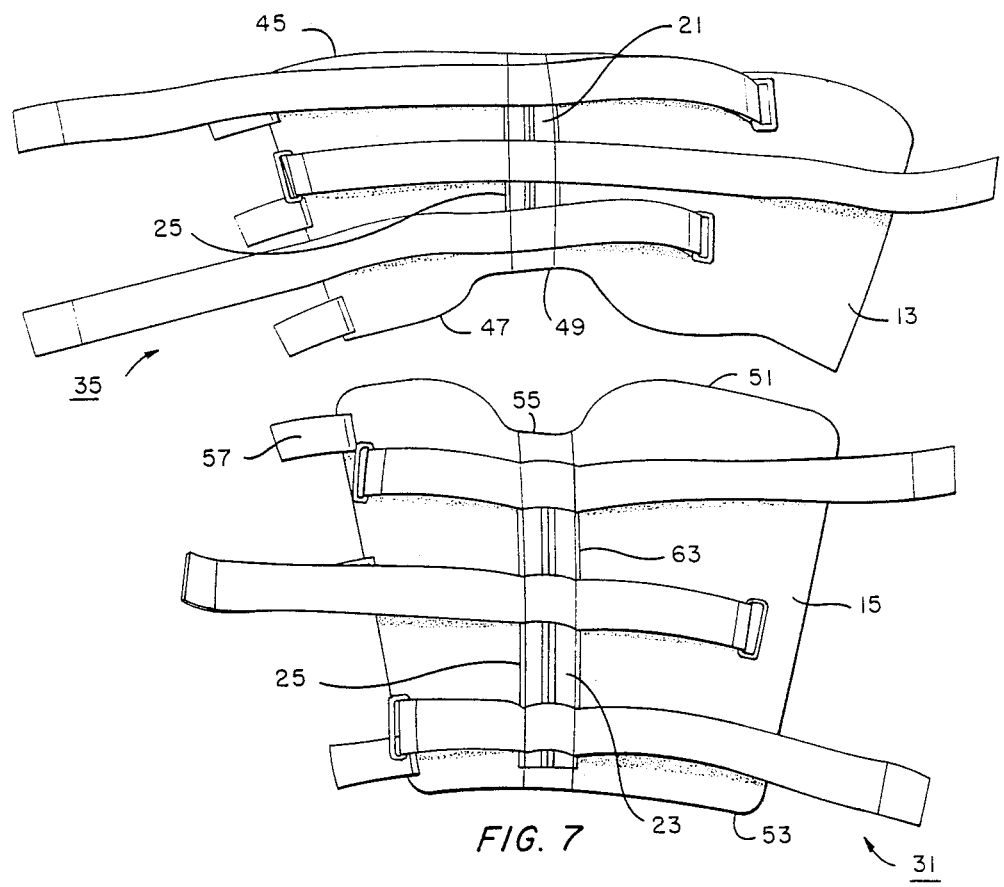
FIG. 6
FIG. 7
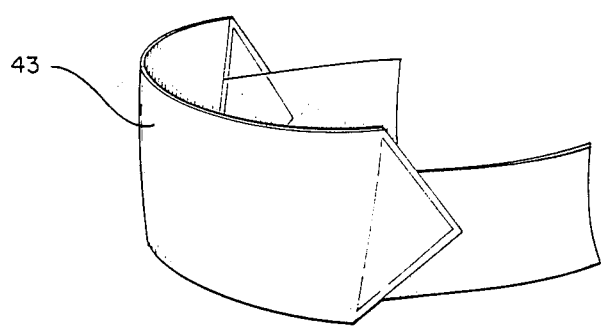
FIG. 8

UNIVERSAL LEG BRACE SYSTEM

FIELD OF THE INVENTION

This invention relates generally to a universal leg brace system for controlling the degree of motion which is permitted between the proximal and distal members of a wearer's lower limbs. More particularly, it relates to a universal leg brace system having a hinge device adjacent a knee and having significant structural support longitudinally of the leg members so as to allow selectively controlling the amount of motion permitted between the leg members and enable using the lightweight universal leg brace system instead of a heavy, totally enclosing leg cast or the like.

BACKGROUND OF THE INVENTION

It is well known in the prior art to externally support injured limbs of a person to foster healing. It is routinely employed by orthopedic specialists in treating bones, joints and connective tissue by use of external casting, splints, wraps and braces until the body's natural healing processes have been started or completed. When the injury involves a person's legs, extra problems arise because of the supportive functions which the legs must provide, as well as the very special construction of the knee whose multi-centered pivotal motion allows the tibia to be bent with respect to the femur through a controlled angle.

The old practice of treating a knee injury by placing most of a leg in a rigid cast and leaving it in place for weeks is now being discarded by many surgeons in favor of short term casting. Specifically, it is recognized that in some instances, a lightweight, removable and adjustable combination can be employed as a replacement for a cast; ab initio or after a shortened healing period. Expressed otherwise, this employment can be either instead of a primary cast if the leg injury is not severe or replacement for a primary cast where early healing has started. Ideally, a patient's leg should be immobilized for the shortest feasible period of time and a longitudinally supportive brace and knee hinge allow some degree of exercise for the patient's muscles. This prevents atrophying and prevents the muscles becoming unreasonably weak through lack of use.

In a co-pending application entitled "BRACE FOR ARTICULATED LIMBS", inventor Gary R. Bledsoe, filed Jan. 22, 1981, Ser. No. 227,381, incorporated herein by reference, there was described an improved system of external bracing apparatus for controlling the degree of motion permitted by a wearer's knee and in that application there was delineated the prior art devices and the various approaches, including United States patents that dealt therewith.

Despite that improvement, however, there persists a need for a temporary, removable, adjustable universal external leg brace system that can provide greater support peripherally and longitudinally of the leg members through the use of greater stiffening and the like.

In the file history of that patent, there is included a prior art statement which lists a variety of patents ranging from the so-called Knee Immobilizers, through the Polio Braces to the Knee Braces or Supports. The group of knee immobilizers included the following U.S. Pat. Nos. 3,853,123; 3,935,858; 4,013,070; 4,041,940; 4,090,508; and 4,111,194. All these patents are distinguishable from this invention in that they do not have a hinge and no suggestion as to how they can be employed with a hinge.

The so-called Polio Braces are exemplified by the following U.S. Pat. Nos. 2,632,440; 2,943,622; 3,826,251; 3,827,431; and 3,844,279. These patents describe devices that are intended for long term wear over years, rather than short term rehabilitation of an injured knee or the like. These types of prior art apparatuses are usually recognizable by an attached shoe which constitutes a permanent part of the brace. Another identifying feature is a pair of load bearing members (usually steel) that extend vertically for the full length of the brace and which serve to support a leg and torso during standing or walking.

Inventions in a third category of braces known as Knee Braces or Supports are more nearly pertinent in that they include structures that are designed to support the knee or restrict knee movement to foster healing. The hinge may or may not be adjustable so as to control the degree of movement of these knee braces or supports. Exemplary of this type are the following U.S. Pat. Nos. 3,575,166; 3,581,741; 3,669,105; 3,785,372; 3,786,804; 4,136,404; 4,220,148; 4,233,967 and 4,241,730. A few comments are given with regard to these individual patents since they are more nearly pertinent to this invention. U.S. Pat. No. 3,575,166 includes two rigid cuffs that partially encircle a person's thigh and calf, respectively encompassing about 270° of the wearer's leg member. The remaining 90° gap is filled by flexible elastomeric material. A single hinge is rigidly connected at one side of the thigh and the calf cuffs in order to provide at least some control with regard to a person's movements. U.S. Pat. No. 3,581,741 discloses similar "body portions" 18, 28 which are described as being made of tough, polymeric, plastic material which may be internally reinforced with glass filaments or the like. While such rigid "body portions" may be advantageous in some cases, they do not provide the flexibility that is inherent in this invention and they require multiplicity of different sizes. The patentee recognized this deficiency and attempted to compensate by providing inflatable bladders within his rigid shells for filling the space between the rigid shells and the patient's leg. U.S. Pat. No. 3,669,105 discloses a construction which has at least been manufactured and sold. It is commonly referred to as the "Lennox Hill Brace". This is the type of brace that has been worn more or less successfully by athletes such as Joe Namath in order to prevent rotation of a weakened knee.

U.S. Pat. No. 3,785,372 is a rather complicated hinge applicance that is adapted to be attached to a person's leg through upper and lower casts. There is no disclosed technique for temporarily removing the Craig applicance of this patent for either medical or personal reasons. U.S. Pat. No. 3,786,804 has a single-piece cylindrical sleeve of elastic material that is described as being dimensioned to accommodate the wearer's knee. However, it is not apparent how a single cylindrical sleeve might be ideally suited for a large man or woman or a small child. Moreover that patent describes loose mounting of hinges so that it leaves a lot to be desired compared to this invention. U.S. Pat. No. 4,136,404 discloses an apparatus specifically intended to be connected to sides of a ski boot and is not very pertinent to this invention. U.S. Pat. No. 4,220,148 discloses what may indeed be a "stabilizer", but it is not the structural kind of apparatus of this invention. That patent does not disclose cushion sheets, elongate braces that lie on either side of the wearer's knee a plurality of straps and the other support in accordance with this invention. U.S. Pat. No. 4,233,967 discloses a construction made entirely of plastic so that it will be immune to liquids that might otherwise contribute to corrosion. That patented device does not have the structural elements recited in this invention. U.S. Pat. No. 4,241,730 discloses a knee support which includes a pair of pivotally interconnected rigid braces but does not include elongate braces, cushion sheets, straps and other elements of this invention.

While all of these various devices of the prior art may have solved one or more special problems, none of them offer the versatility that has been desired by doctors and patients to foster healing, provide comfort and alleviate the need for heavy primary casts and the like.

SUMMARY OF THE INVENTION

Accordingly, it is an object of this invention to provide a universal leg brace system for controlling the motion of a knee in a person's legs and obviating a primary cast to provide longitudinal structural support.

Another object is to provide a universal leg brace system that is capable of being quickly and easily applied, that provides longitudinal and circumferential support so that it can be used to replace a primary cast system once healing is started or to obviate the necessity for one if the injury is not so severe.

These and other objects will become apparent from the descriptive matter hereinafter, particularly when taken in conjunction with the appended drawings.

In accordance with one embodiment of this invention, there is provided a universal leg brace system for providing support and controlling the degree of motion permitted by a wearer's knee and adapted to be affixed so that it lies partly above and partly below the wearer's knee while positioning a hinge correctly on both sides of the wearer's knee. The universal leg brace system comprises:
  a. first and second flexible sheets of cushioned materials adapted for being snugly wrapped around the wearer's thigh and calf;
  b. first and second pairs of elongate braces for being positioned respectively on opposite sides of a person's thigh and calf;
  c. at least first and second pairs of rear stays adapted for being connected with a flexible sheet for providing posterior structural support in the longitudinal direction posteriorly of the person's thigh and calf;
  d. means for connecting the first and second pairs of rear stays with the first and second flexible strips;
  e. tibial and femoral plates adapted for being connected respectively with the first and second flexible sheets on the anterior portion of the leg adjacent the tibia and femur for providing significant longitudinal structural support;
  f. means for adjustably positioning the respective pairs of braces, plates and the like around the wearer's leg members with the hinge properly positioned adjacent the wearer's knee and connected with the braces; and
  g. strong straps.

The width of each of the flexible sheets is sufficient to circumferentially envelope at least most and preferably all of its associated leg member. The length of each sheet is sufficient to encompass at least half the length of its respective leg member. Preferred cushioning material is bonded to a sheet of pile-type material having sufficient "nap" to serve as an anchor for resilient hooks of the Velcro type. The braces are relatively stiff so as to resist torsion and bending loads and provide structural support on the side. Preferably, as will be described in more detail, the elongate braces consist of structural cores that are enclosed in non-metallic sheets of vinyl or the like and are bonded to the sheets in order to inhibit relative movement between the sheets and the interior cores. Pads of resilient hook material are attached to the outer surface to facilitate being selectively positioned to and engage the flexible sheets. The rear stays are preferably affixed immovably with respect to the respective sheets for providing significant structural support when encircled by straps to be held firmly in place and prevent any bending. Similarly, the respective tibial and femoral plates are placed on the anterior portion of the leg adjacent, respectively, the tibia and the femur and are connected with the respective sheets. The respective plates provide significant longitudinal support when encircled by straps. The straps encircle the leg circumferentially and hold all the respective elements about the thigh and the calf, respectively so as to provide encompassing and longitudinal structural support.

A plurality of accoutrements, such as a connected shoe insert and a weight bearing brim, add flexibility.

BRIEF DESCRIPTION OF THE DRAWINGS

FIGS. 6 and 7 are plan views, of the unfolded flexible sheets for encompassing, respectively, the thigh and calf and forming a part of the universal leg brace system of FIG. 1.

FIG. 8 is an excercise cuff of the universal leg brace system of FIG. 1.

DESCRIPTION OF PREFERRED EMBODIMENT(S)

One of the main advantages of this invention is that the total combination of the universal leg brace system comprises a plurality of elements that co-act to provide both circumferential support and longitudinal support. While the invention may be useful in other areas, it will be described hereinafter with respect to being employed on a leg or the like as a replacement for a permanent type cast. It is to be borne in mind that this replacement may be in the place of, if the injury is amenable to this as determined by the physician, or as a replacement when the cast is removed, after healing is started, again at the option of the physician.

Figure 1:
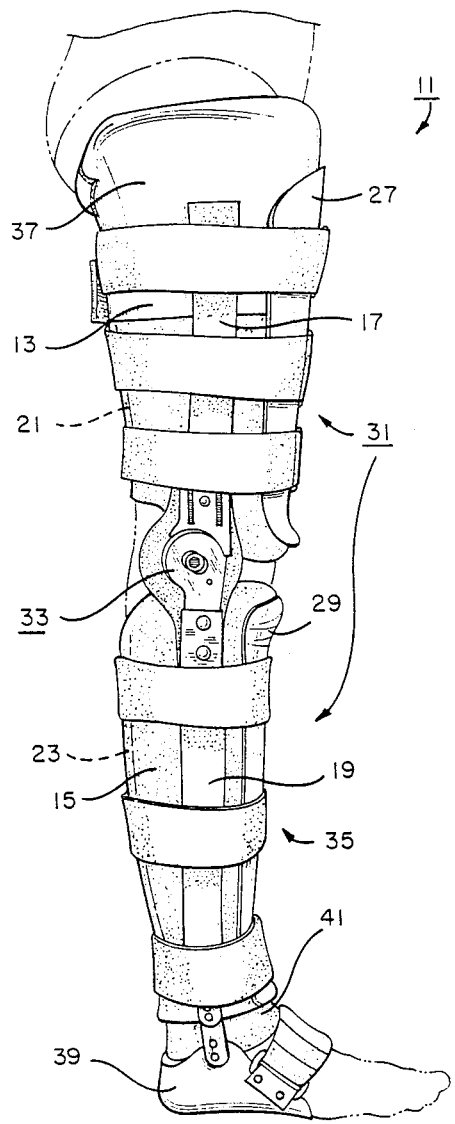
FIG. 1 is a partial side elevational view of a leg encompassed within the universal leg brace system in accordance with one embodiment of this invention.
Figure 2:
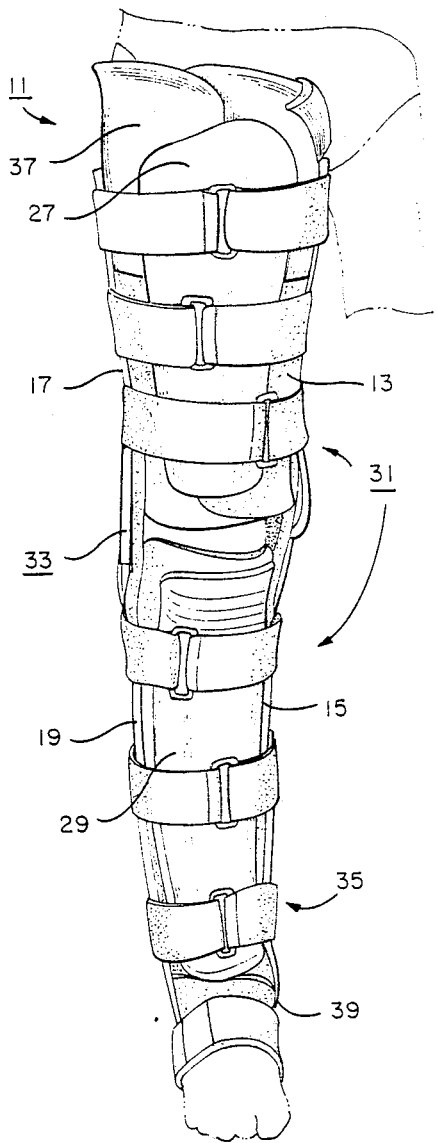
FIG. 2 is a partial front elevational view of the universal leg brace system of FIG. 1.
Figure 3:
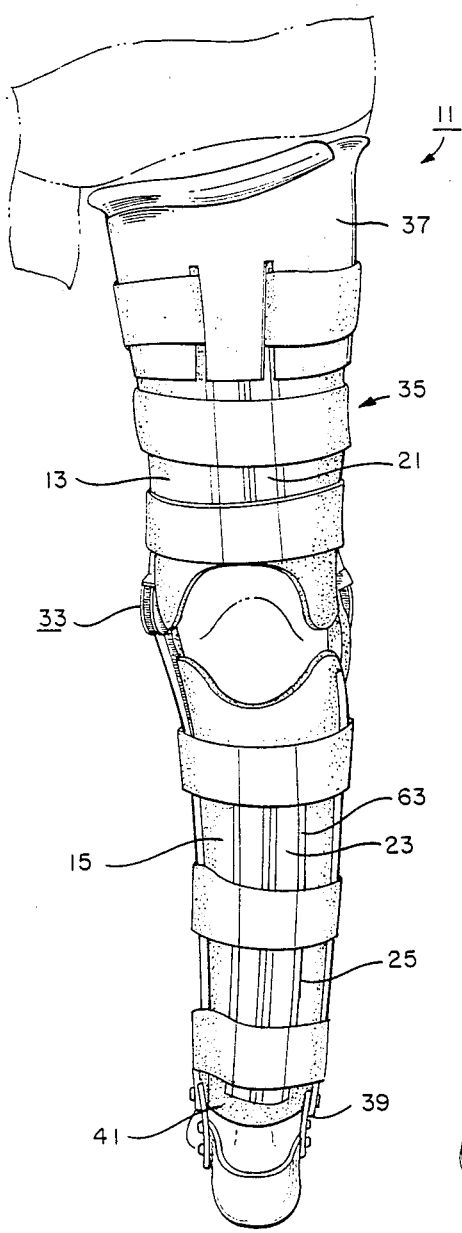
FIG. 3 is a rear elevational view of the univeral leg brace system of FIG. 1.
Figure 4:
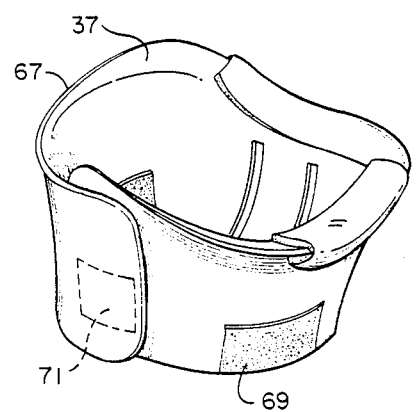
FIG. 4 is an isometric view of the weight bearing brim of the universal leg brace system of FIG. 1.
Figure 5:
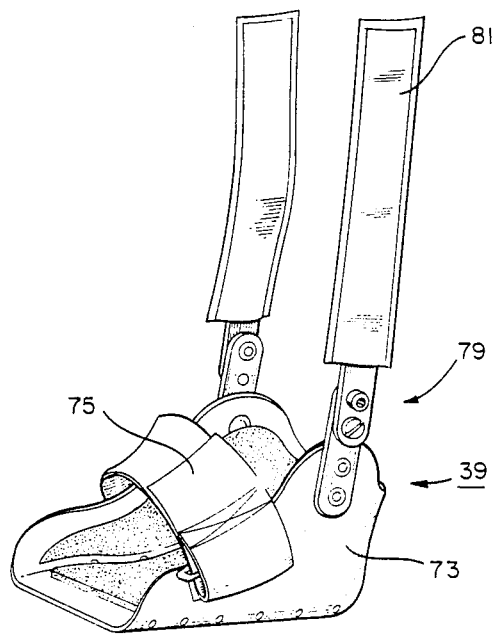
FIG. 5 is an isometric view of the shoe insert of the universal leg brace system of FIG. 1.

Referring to the figures, the universal leg brace system 11 is illustrated in FIGS. 1–3. The universal leg brace system 11 includes at least the first and second flexible sheets 13, 15, FIGS. 1–3, 6 and 7; first and second pairs of elongate braces 17, 19, FIGS. 1,2,10 and 11; at least first and second pairs of rear stays 21,23, FIGS. 1, 3 and 6; means 25 for connecting the rear stays with, respectively, the first and second flexible sheets 13, 15, FIGS. 3 and 6; tibial and femoral plates 27, 29, FIGS. 1, 2, 12 and 13; means 31, FIGS. 1, 2, 6, 12 and 13, for adjustably positioning and selectively attaching the pairs of elongate braces and plates to the first and second sheets 13, 15; hinge means 33, FIGS. 1–3, 10 and 11, for controlling the degree of flexion and extension of the leg. Preferably, a plurality of strong straps 35, FIGS. 1–3, 6 are provided and adapted to be wrapped circumferentially around the wearer's leg to hold the combination together for support. Also provided are other accoutrements such as the weight bearing brim 37, FIGS. 1–3 and 4; shoe insert 39, FIGS. 1–3 and 5 and an ankle cuff 41, FIGS. 1, 3 and 9. If desired, exercise kits, such as cuff 43, FIG. 8, can be provided.

Respective elements of the combination universal leg brace system 1,1 will now be discussed individually.

The first flexible sheet 13 of cushioned material is adapted for being wrapped snugly around the wearer's thigh. A preferred flexible material is medium-density, open-cell polyurethane foam having a thickness of about three-eights inch ($\frac{3}{8}$"). The preferred material is sufficiently porous to prevent sweating under normal conditions. It is lightweight. It will not usually cause an allergic skin reaction. It is contourable to match a person's leg; and it is capable of being washed (as required) without losing its shape or structural integrity.

The length of the flexible sheet 13 will normally be sufficient to encompass more than half of the length of the wearer's thigh, in order to provide a substantial "anchor" for the remainder of the elements that will be connected therewith. A preferred length is about thirty centimeters 30 cm.). The top edge 45, FIG. 6, of the first flexible sheet 13 will normally be relatively straight, while the bottom edge 47 will normally have a bell-shaped recess 49 near its center in order to preclude interference with the back of the leg or another part of the apparatus 11 when the leg is bent.

The second flexible sheet 15 of cushion material is similar to the first sheet 13 but is provided for snugly wrapping around the wearer's calf. The second sheet has a length which is sufficient to encompass more than half the length of the calf; preferably, all of it. To create a universally useable calf piece, the second piece 15 is about fifty centimeters (50 cm.) wide along its top edge 51 and somewhat less; for example, about thirty-five centimeters (35 cm.); along its bottom edge 53.

The bottom edge 53 of the second flexible sheet 15 is substantially straight; whereas the top edge 51 has a bell-shaped recess 55 near its center to alleviate any problems with interference when the leg is bent. The second sheet 15 has a length sufficient to encompass more than half the length of the wearer's calf in order to provide a substantial anchor. A preferred length is about forty centimeters (40 cm.).

The first and second flexible sheets 13, 15 have a pile, such as a polyester pile which is adapted to serve as a medium for engaging the resilient hooks of the type commonly employed in the fasteners of the Velcro fastener. By use of a bonded pile/foam material, it is possible to manufacture relatively standard sized sheets that are big enough to wrap circumferentially around essentially all adult legs. The soft material can be easily cut with scissors, also, and sized to fit a small child or the like. The first and second flexible sheets will have one side having no tabs or fasteners so excess material can be trimmed from that edge or side. For example, a first flexible sheet may have width dimensions along the top edge 45 of about seventy centimeters (70 cm.) and a bottom edge of about fifty-five centimeters (55 cm.) but trimmed to any desirable width to get the desired encompassing of the thigh. In like manner, the second flexible sheet can be trimmed along its one edge where there are no tabs.

On both the first and second flexible sheets 13, 15, there are provided at one edge such as the left edge in FIG. 6, a plurality of short tabs 57 of the hook-type fastener material, commonly known as Velcro. These tabs 57 may be varied in number, typically there will be two or three of them on each piece, and used to initially position the respective pieces 13, 15 around the wearer's leg members. The tabs 57 will be buttressed by strong straps so are not required to resist significant loads which may eventually be placed on the apparatus and may be relatively small to conserve material and minimize cost. Ordinarily, the tabs 57 are employed temporarily to hold a sheet in position while other connecting and fastening means are engaged From the foregoing, it can be readily seen that the flexible sheets 13, 15 may be selectively removeable and replaceable around the wearer's leg members for personal hygiene, tightening in the event of swelling diminishing, or the like.

The first and second pairs of elongate braces 17, 19 are relatively stiff so as to resist both torsion and bending loads. The first pair of elongate braces 17 are adapted to lie on opposite sides of the wearer's thigh. The second pair of elongate braces 19 are adapted to lie on opposite sides of the wearer's calf. A preferred structural material for the core of the elongate braces 17, 19 is an elongate piece of aluminum, such as 6061 aluminum, having a width of about two centimeters (2 cm.) and a thickness of about three millimeters (3 ml.). The first and second pair of elongate braces have respective central ends 59, 61, FIGS. 10 and 11, that are connected with the hinge means 33. The respective first and second pairs of elongate braces may be made in standard size length and readily clipped to size, or they may be made in specific sizes for specific height persons. For example, the length of two end to end braces 17, 19 may be sized from about fifty-six centimeters (56 cm.) for a small person to about seventy-six centimeters (76 cm.) for a relatively tall person. The respective braces 17, 19 have an envelope, or sheet, secured to the structural core. Each envelope, or sheet, has an interiorly facing surface with a substantial quantity of Velcro-type hook material protruding therefrom. The resilient hooks are provided so that a brace may be secured to the outer pile surface of the first and second flexible sheets 13, 15 at essentially any desirable location. That is, the cut pile outer surface of the sheets 13, 15 can be wrapped around any size leg and still provide a base for receiving a hook type pad on the elongate braces. Ordinarily, the proper placing of elongate braces is that which provides the proper location of the hinge means 33 on each side of the wearer's knee. The proper location of such a hinge is described in an article by Dr. Augusto Sarmiento entitled "Fracture Bracing" which appeared in the July-August, 1974 issue of CLINICALRTHOPE-DICS/ . Another informative article describing a proper placement use of knee braces in an article by Dr. Vert Mooney, et al, entitled "Cast-Brace Treatment For Fractures Of The Distal Part Of The Femur" which appeared in the Dec. 1970 issue of THEOURNAL OF BONE AND JOINT SURGERY/ .

The rear stays 21, 23 of FIGS. 3 and 6, are closely ensconsed in stay pockets 63 which are permanently affixed to the respective first and second flexible sheets 13, 15. For example, the stay pockets are preferably sewn directly to the pile side of the pile-foam sheet. The stay pockets 63 are typically made of easily cleanable material such as vinyl plastic. The stays which are enclosed within the stay pockets 63 are preferably not too wide and a plurality of the stays are employed peripherally in order to provide substantial longitudinal and peripheral support, yet conform as closely as possible to the thigh. For example, a width of about 2 centimeters (2 cm.) is probably about as much as would be desirable for any given stay. As illustrated, two side-by-side stays 21, 23 are permanently affixed to the first and second flexible sheets, respectively in pockets near the center of the universal leg brace system 11 at its rear when it is wrapped around its respective leg member. It is preferred to employ seams down each of the respective stay pockets 63 and separate the respective pairs of rear stays. Thus it can be seen that the stay pockets serve as a means for connecting the respective pairs of rear stays with the first and second flexible sheets.

The tibial and femoral plates 27, 29, FIGS. 1, 2, 12 and 13 are connected respectively with the first and second flexible sheets by means 31 so that they can be respectively adjustably positioned and selectively held in place on a temporary basis until the straps can be affixed. Specifically, the means 31 comprise respective strips of Velcro 65, FIGS. 12 and 13 so that the respective plates can be pushed into their position and into engagement with the pile exterior on the respective first and second flexible sheets 13, 15 to be temporarily held in place until the straps can be added.

The femoral and tibial plates are relatively rigid and are preformed to cover the anterior of the thigh and calf of the leg anteriorly of the femur and tibia, respectively. This serves as a form of protection analogous to that provided by a permanent type cast so that the leg would not be injured if it is bumped into an object as the wearer moves through furniture or the like. Moreover, the respective femoral and tibial plates 27, 29 are designed to provide significant longitudinal support, as well as peripheral support for the respective leg members once they are strapped into place. As illustrated, the respective tibial and femoral plates are formed of a rigid plastic. Typical of the rigid plastics that can be employed are polyethylene, polypropylene, polyvinyl-chloride, and acrylonitrile butadiene styrene (ABS) copolymer. The respective plates are designed to fit conformingly as closely as possible with the respective first and second flexible sheets which are contoured to their respective leg members. As illustrated, the respective tibial and femoral plates are available in the plurality of different sizes for different sized leg members. As with the respective flexible sheets, the respective plates are sufficiently long to cover more than half the length of their respective leg members.

Specifically, the tibial plate 29 is used for support and for providing secondary bracing when a tibial fracture is present. It provides contour support of the tibia and anteromedially and anteriorly and distributes the pressure evenly to aid in prevention of edema. In the commercial embodiment it is available in small, medium, large and extra large sizes for respective brace sizes ranging from twenty-two inches (55 centimeters) to as long as thirty-four inches (86 centimeters).

The femoral plate 27 is used for providing secondary bracing of mid-shaft and distal femoral fractures to provide even pressure distribution and support while aiding in preventing edema. It is available in small, medium and large sizes for brace lengths running from twenty-two inches (55 centimeters) to thirty-four inches (86 centimeters).

The hinge means 33 is, as indicated hereinbefore, attached to the respective central ends of the braces and adapted to lie on opposite sides of the wearer's knee. Preferably, the hinge has a control in order to control the angle that is formed between the brace members for controlling the degrees of flexion and extension of the leg. There are several such hinge means 33 commercially available, including both simple hinges and polycentric hinges. A preferred type hinge is that describe in co-pending application Ser. No. 473,229, filed Mar. 8, 1983, now U.S. Pat. No. 4,489,718, Kelsey Martin, inventor, assigned to the assignee of this invention. That hinge provides the currently preferred polycentric type hinge which more nearly approximates the exact motion of the human knee.

The straps 35 are wrapped circumferentially around all of the respective elements described hereinbefore to bring them into intimate engagement with each other and with their respective leg members. The straps 35 are preferably not stretchable, although if they have a high enough co-efficient of elasticity, a small amount of stretch can be tolerated. The straps must have a strength of being able to withold at least four hundred pounds (400 lbs.) without more than ten percent (10%) elongation, however, in order to have the desired tension to encompass and be selectively attached to the braces, the first and second flexible sheets and to enclose and pull into supporting conformity the respective rear stays and the respective plates when wrapped circumferentially therearound; and in order to tension by suitable securing means such as a D-ring type buckle as described in the aforementioned Ser. No. 227,381. A preferred type of strapping material is the two inch (5 centimeter) wide strap of non-stretch polyester having an outer surface of cut pile which is bonded to a core of one-eighth inch (⅛ in.) opencell, high-density polyurethane foam. The five centimeter (5 cm.) width for preferred strap 35 provides a means for distributing loads onto a leg member over an area that is sufficiently large to minimize discomfort to the wearer. As indicated, the straps should prevent any risk of failure which might be occasioned by unusual flexing of a muscle or unexpected load occassioned by an accidental fall or the like. Typical of the suitable strapping material is that available from the Ouimet Corporation of Nashville, Tenn., comprising a three-pinch laminated (bonded) strap identifiable as number 2100 polyester pile/one-eighth inch (⅛ in.) polyurethane foam/number 12100 polyester pile strap.

Preferably, the strap is secured to its associated first flexible sheet 13, 15 near the center of the strap with its two free ends being capable of being wrapped around, respectively, the thigh and calf of the wearer. At one of the free ends of a given strap is secured the fastener, such as a D-ring, and the opposite end of the strap has a piece 44 of Velcro-type resilient hook material. Rolls of suitable hook material are commercially available from Ouimet Stay and Leather Company, Brockton, Mass. The hook end is passed through the associated D-ring and then pulled backward in order to create tension in the strap 34 prior to engaging the hooks with the outer napped pile of the surface of the strap 34. It is preferable to have the plurality of the straps alternate in "direction" such that the top and bottom fasteners are on ends which extend in one direction from their anchoring point and the middle strap and its associate fastener extends in the opposite direction. By alternating the direction of pulling on the straps in order to tighten them when installing the apparatus 11, any tendency to unreasonably twist the tibia and femur sections with respect to each other is reduced.

The brim 37 is used to help transmit loads from the gluteal muscles through the brace to the ground. It is used in combination with the femoral plate and the remainder elements of this apparatus for secondary bracing, and particular, for bracing of the femoral fractures and to partially unload the fracture during ambulation. The brim is formed in plurality of sizes. Specifically, as illustrated, the sizes are small, medium and large for respective thigh circumferences in the respective ranges of sixteen inch (16")-twenty inch (20") (51 centimeters); twenty inch (20")-twenty-five inch (25") (63 centimeters); and twenty-five inch (25")-thirty inch (30") (76 centimeters). As with the femoral plates, the weight bearing brim is formed from a stiff, load bearing substance such as metal or plastic. While the load bearing brim may be formed from stainless steel or other non-corrosive material, it is preferably formed from a plastic such as rigid polyethylene, polypropylene, polyvinylchloride or acrylonitrile butadiene styrene (ABS) copolymer. As illustrated, the exterior surface of the weight bearing brim has a plurality of fastening surfaces 69 which co-act with respective fastening tabs 71 on the interior of the end which overlaps for fastening. Either the surface or the tab may comprise the pile material for engaging Velcro while the other will comprise the Velcro material to enable fastening this into desired circumferential engagement before it is supported by the respective other elements described hereinbefore. The brim has a rear slotted tab 85, FIG. 3, for being supported by a top strap 35. For example, the weight bearing brim may be inserted interiorly of the femoral plate, the elongate braces, and the like such that sufficient longitudinal support is provided.

The shoe insert 39 is for foot control, maintaining hinge alignment and maintaining internal and external rotation control. A plurality of types of shoe inserts have been available in the prior art and the particular type of shoe insert is not critical to this invention. As illustrated, the shoe insert generally comprises a foot receptacle 73, FIG. 5, and an adjustable strap 75, similar in operation to the straps 35 described hereinbefore for encompassing the foot. Ordinarily, some sort of hinge means 79 is provided for allowing pivotal movement of the shoe receptacle with respect to elongate braces 81. The hinge means 79 can be tightened to an immobile (non-pivoting) position, if desired. The elongate braces are similar in construction to those described hereinbefore and have the respective external surfaces for being held in place by means of the straps 35 and the second flexible sheet 15.

Figure 9:
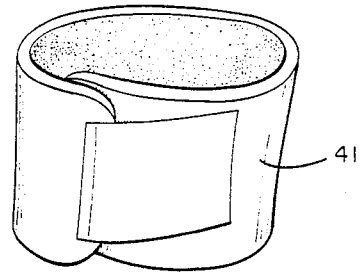
FIG. 9 is an isometric view of an ankle cuff of the universal leg brace system of FIG. 1.
Figure 11:
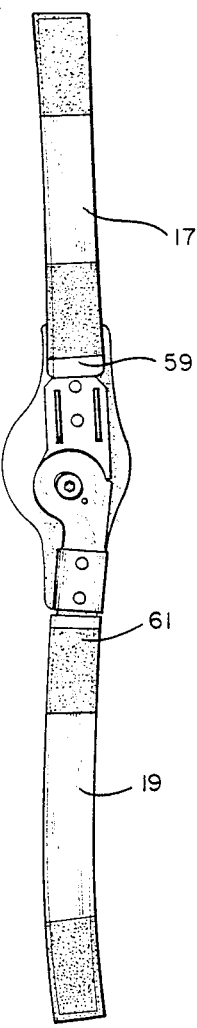
FIG. 11 is a side elevational view of the hinge and connected elongate braces, in the extended position, of the universal leg brace system of FIG. 1.
Figure 10:
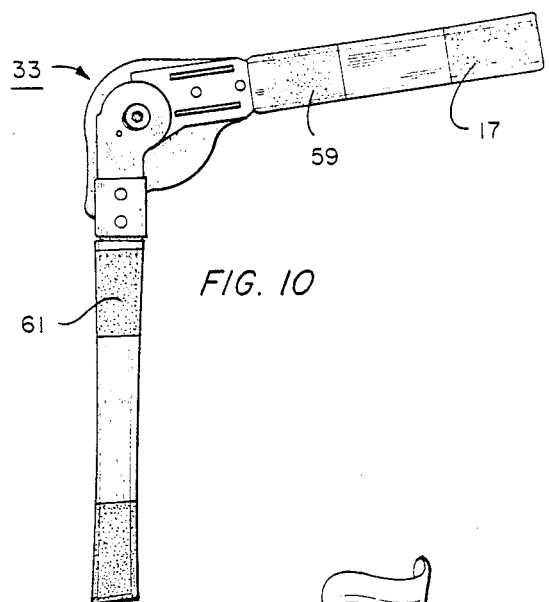
FIG. 10 is a side elevational view of a left side hinge means and attached elongate braces, in the bent position, of the universal leg brace system of FIG. 1.
Figure 12:
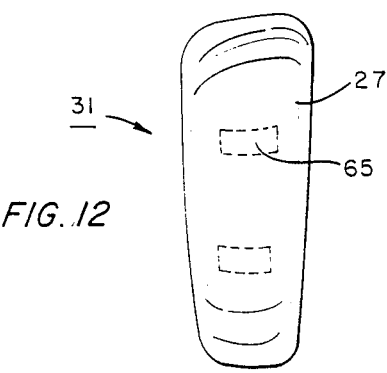
FIG. 12 is a front plan view of the femoral plate of the universal leg brace system of FIG. 1.
Figure 13:
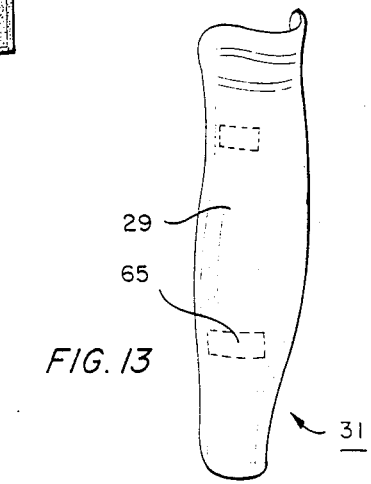
FIG. 13 is a front isometric view of the tibial plate of the universal leg brace system of FIG. 1.

To prevent the normal tendency for the load bearing universal leg brace system 11 to move downwardly, an ankle cuff 41, FIGS. 1, 3 and 9 is provided. Such an ankle cuff 41 ideally consists of foam-pile combinations similar to the material used in the respective first and second flexible sheets 13, 15 and a Velcro-type hook tab secured to one end of the strap so as to permit a single size strap to be affixed to most any person's ankle. The ankle cuff 41 provides a slightly bulbous but comfortable object at the bottom of the apparatus 11 so that any downward movement will be restricted. A small pad of Velcro hooks may advantageously be sewn to the bottom of the calf section, or second flexible sheet 15, so that it may engage the outer nap on the cuff 41 as a way of inhibiting any downward movement.

Of course, excercise straps, or cuff, 43, FIG. 8, can be employed as desired for attaching weights and the like.

In operation, the universal knee brace system is applied as follows. First the leg is measured and the size in accordance with a chart provided by the manufacturer, Medical Designs, Inc., Arlington, Tex., is employed to select the size of the respective elements. Failure to correctly size the braces or other elements may result in slippage and poor support. Next the ankle and calf cuff and second sections are snugly applied, respectively by wrapping the ankle cuff 41 around the ankle snugly. The second flexible sheet is also wrapped snugly around the calf, or at least covering half of the medial malleoleus. The calf section stays are centered on the back of the calf with the knee cut out positioned for unrestricted motion at the knee and ankle. The quick tabs 57 are fastened first to contour into the desired shape followed by the remaining quick tabs being fastened. Next the thigh section is fastened. The thigh sections has the stays on the back of the leg with the knee cut out positioned to allow unrestricted knee motion. Again the center quick tab 57 is fastened and the remainder of the first flexible sheet contoured to fit the thigh snugly and then the remaining quick tabs are fastened. The cut out section at the knee should enable placing the hand behind the knee to check for proper clearance.

Preferably, the brace arm, or elongate braces, are contoured somewhat to the leg's shape and then the hinge center means 33 is aligned with the femoral epicondyles (in line with the center of the patella) two-thirds posteriorly from patella to back of knee. The longest brace arm is the tibial end.

Next the straps and brace arms are interlocked. Working from bottom to top, pull the straps firmly toward the brace pressing arms. Be certain that the pile straps engage hook pads on each of the brace arms, or elongate braces. Loop the strap through the D-ring, pull back to tighten and press the hook tab to the strap in the illustrated embodiment. Do this sequentially until the top has been fastened.

Next the hinges are set to facilitate the desired degree of flexion and extension to be allowed. In conventional prior art type hinges, respective dials are turned to the desired settings and respective hex nuts or the like tightened into place. In the embodiment described in the aforementioned U.S. Pat. No. 4,489,718, an Allen wrench is used to position indicators and restrict movement of the cam through only the desired degree of flexion and extension.

The tibial and femoral plates are then emplaced on the anterior exterior of their respective flexible sheets anteriorly of the wearer's tibia and thigh by means 31. The tibial and femoral plates 27, 29 are temporarily and adjustably positioned until they can be encompassed by the straps.

If the brim is installed, it should be installed as indicated hereinbefore and then the completed universal leg brace system 11 checked to see that the position of the hinge is correct and that the proper contouring of the respective stays, tibial and femoral plates, elongate braces and the like are attained.

For easy removal, the straps are simply undone and the plates removed while unfastening the quick tabs inversely to that described with respect to the assembly.

Where the shoe insert is employed, it is slipped on and fastened; and the aligned arms contoured and fastened into position similar with the other elongate braces by being temporarily placed followed by having the straps tightened therearound. If an adjustable hinge means is employed, suitable wrench and screws are provided to permit or prevent, as desired, pivotal movement at the ankle of the patient. As is well recognized, passive internal or external rotation, dynamic rotation or torque or the like can be employed with a shoe insert.

The tibial plate is correctly positioned by centering the tibial plate and pressing it into position on the front of the brace before the straps are put into their tightened, encompassing position. Again, the straps are tightened working from the bottom to the top. The top of the tibial plate should terminate just below the knee.

In similar manner, the femoral plate is positioned and pressed into its temporary position before the straps are tightened. The hips should be flexed and check for clearance at the groin area before the straps are tightened into position. If the brim is to be employed, it should be emplaced and checked before tightened. Thereafter, the straps are tightened from bottom to top. The bottom of the femoral plate should terminate above the knee to allow flexion of the knee and should not cause binding in the groin, or perineal area.

In employing the brim, the correct size is selected by measuring the thigh circumference at the upper region where the brim will be positioned. Next the upper thigh contour straps are passed through the two rear slots on the brim. The thigh section should be contoured around the interior of the brim. The hook pad on the brim should firmly engage the thigh section and the combined unit slipped onto the patient. Check to see that the back stays are centered on the back of the thigh and the square side of the brim rests on the relaxed gluteal muscle. Contour the thigh section around the leg and fasten the three quick tabs. Pull front opening of the brim together and press firmly to engage.

As always with any brace system, it should be checked to observe that the back of the brace is supporting the weight when the patient is walking. It should be ascertained that the upper straps firmly engage the brace arms and the brim and comfort should be checked.

One of the advantages of this invention is the modular concept in which a variety of combinations of elements can be employed for respective purposes. For example, a tibial fracture may necessitate only the second sheet, lower braces, shoe insert, stays, tibial plate and straps. Another of the advantages of this invention is that respective exercise pads or kits can be readily employed; for example, for Dorsey-Flexion Exercise, for Planter-Flexion Exercise, Flexion Exercise or Extension Exercise. Moreover, control rototary instability dynamic exercise can be employed and suitable straps affixed for controlling anterior subluxation of the knee. Moreover, various traction apparatuses are easily connected with the universal leg brace system of this invention.

From the foregoing descriptive matter, it can be seen that the object delineated hereinbefore are realized with this lightweight, universal leg brace apparatus 11. Specifically, this apparatus of the universal leg brace system 11 will weigh only half or less of what most cast braces have weighed in the past. Moreover, this universal leg brace system 11 is economical and may be used only a single time by a single patient or multiply if necessary.

Although this invention has been described with a certain degree of particularity, it is understood that the present disclosure is made only by way of example and that numerous changes in the details of construction and the combination and arrangement of parts may be resorted to without departing from the spirit and the scope of the invention, reference being had for the latter purpose to the appended claims.

What is claimed is:

1. A universal leg brace system for supporting and controlling the degree of motion permitted by a wearer's knee, comprising:
   a. first and second flexible sheets of cushioned material, one of which being adapted for snugly wrapping around the wearer's thigh and the other being adapted for snugly wrapping around the wearer's calf, the width of each sheet being sufficient to circumferentially envelop at least most of its associated leg member, the length of each sheet being sufficient to encompass more than half the length of its respective leg member; said flexible sheets being selectively removeable and replaceable around the wearer's leg member;
   b. first and second pairs of elongate braces, each of said braces being relatively stiff so as to resist both torsion and bending loads, said first pair of elongate braces being adapted to lie on opposite sides of the wearer's thigh and the second pair of elongate braces being adapted to lie on opposite sides of the wearer's calf;
   c. at least first and second pairs of rear stays adapted for being connected respectively with said first and second flexible sheets for providing posterior structural support in the longitudinal direction; said first pair of rear stays being adapted to provide posterior structural support in the longitudinal direction along the posterior of the thigh; said second pair of rear stays being adapted to provide posterior structural support in the longitudinal direction along the posterior of the calf;
   d. means for connecting said first and second pairs of rear stays with said first and second flexible strips;
   e. tibial plate adapted for being connected respectively with said other flexible sheet around the wearer's calf for providing anterior structural support in the longitudinal direction; said tibial plate being adapted to provide anterior structural support in the longitudinal direction along the anterior portion of the calf;
   f. means for adjustably positioning and selectively attaching said first and second pairs of elongate braces to said flexible sheets and said tibial plate to the exterior sides of said other sheet after said sheet has been wrapped around the wearer's calf leg member, said braces having central ends which are near one another when respective sheets are wrapped around their respective associated leg members and the braces are attached to the respective sheets;

g. hinge means attached to respective central ends of said braces and adapted to lie on each side of the wearer's knee; said hinge means being effective for controlling the angle that is formed by the two braces on a given side of the wearer's leg; and h. a plurality of strong straps which are selectively attached to said braces and encompass respective said braces, rear stays and plates and which are adapted to be wrapped circumferentially around the wearer's respective leg members; said straps having connection means so that they can be placed in tension around the wearer's leg and secured to said braces and hold in place said braces, rear stays and plates for providing substantial structural support without the necessity of a totally encompassing leg cast;

i. a femoral plate adapted for being connected with said one of said flexible sheets and for providing anterior structural support in the longitudinal direction along the anterior portion of the thigh of the wearer; said femoral plate being adapted to be encompassed by said straps about said thigh of a wearer; and j. means for at least temporarily connecting said femoral plate with said one of said flexible sheets snugly wrapped around the wearer's thigh; said means for attaching said femoral plate being means for adjustably positioning and selectively attaching said femoral plate prior to being encompassed by said strong straps.

2. The universal leg brace system of claim 1 wherein said tibial and femoral plates are formed of a rigid load bearing material and are contoured to closely fit the anterior of their respective leg members.

3. The universal leg brace system of claim 1 wherein the first and second flexible sheets are trapezoidal shaped, and the top parallel edge of the thigh sheet is about 70 centimeters wide, and the shorter parallel edge of the calf sheet is about 35 centimeters wide, and the two adjacent sides of the thigh and calf sheets each have a substantially bell-shaped recess near their centers, whereby the two flexible sheets do not interfere with one another even when the wearer bends that leg upon which the sheets are wrapped.

4. The universal leg brace system of claim 1 wherein at least a major portion of the exterior surface of the first and second flexible sheets consist of soft, pile-type material which is capable of being engaged and held by a plurality of resilient hooks, and wherein a substantial portion of the inside of the surfaces of the pairs of elongate braces have affixed thereto pads of resilient hooks, whereby the elongate braces may be selectively positioned at essentially any appropriate place on the sides of the flexible sheets by engaging the resilient hooks with the sheets after said sheets are wrapped around a respective associated leg member.

5. The universal leg brace system of claim 1 wherein the connecting means associated with the straps constitutes a soft pile-type material fixed to the interiorly facing surfaces of the straps and there are pads of exteriorly facing resilient hooks permanently affixed to the elongate braces whereby the straps are adapted to be secured to the elongate braces by manually forcing together the confronting resilient hooks and the pile-type material.

6. The universal leg brace system of claim 1 wherein each of the elongate braces consist of a structual core enveloped in a non-metallic protective sheet, and the structual cores are permanently bonded to their associated sheets, whereby the structural cores may be held in a supportive position adjacent the leg member by virtue of securely holding their associated sheets.

7. The universal leg brace system of claim 1 wherein the cushioned material in the first and second flexible sheets constitutes an open-cell, medium-density polyurethane foam having a thickness of at least 6 millimeters, whereby such support as is provided by the elongate braces is passed to the leg through an appreciable quantity of cushioned material.

8. The universal leg brace system of claim 1 wherein the combined length of two end-two-end braces lie within the range of 56–76 centimeters, and the weight of the entire apparatus is approximately 18 grams per centimeter of end-two-end brace lengths.

9. The universal leg brace system of claim 1 wherein the plurality of straps are permanently anchored to their respective flexible sheets near a mid-point of said straps, whereby each strap has an interior connection to its sheet and has two free ends which are selectively engageable to hold the sheet around its leg member.

10. The universal leg brace system of claim 1, further including a plurality of temporary positioning tabs made of resilient hook material affixed to a side edge of each of the flexible sheets, and said tabs are selectively engageable with the exterior surface of their associate sheets, and said tabs are effective to hold the respective sheet in place around an associated leg member while elongate braces and straps are being positioned at the proper places in order to complete the installation of the apparatus on the wearer's leg.

11. The universal leg brace system of claim 1 wherein there are at least two pairs, respectively, of the first and second rear stays.

12. The universal leg brace system of claim 10 wherein said rear stays are ensconsed in respective stay pockets on the exterior of said respective said first and second sheets.

13. A tibial fracture walking brace module of a universal leg brace system for supporting a lower leg member of a wearer suffering a tibial fracture, comprising:

a. shoe insert with load bearing uprights connected therewith;

b. a flexible sheet adapted for snugly wrapping around the wearer's calf, the width of the sheet being sufficient to circumferentially envelop at least most of the calf of the wearer, the length of the sheet being sufficient to encompass more than half the length of the calf of the wearer, said flexible sheet being selectively removable and replacable around the wearer's calf leg member;

c. a pair of elongate braces being relatively stiff so as to resist both torsion and bending loads and to provide significant longitudinal and structural support, as well as circumferential support; said braces being adapted to be connected with said uprights on said shoe insert and being adapted to lie on opposite sides of the wearer's calf;

d. rear stays adapted for being connected respectively with the flexible sheet for providing posterior structural support in the longitudinal direction;

e. means for connecting said rear stays with said flexible sheet;

f. tibial plate adapted for being connected respectively with said flexible sheet around the wearer's calf for providing anterior structural support in the longitudinal direction; said tibial plate being adapted to provide anterior structural support along the anterior portion of the calf of the wearer; means for adjustably positioning and selectively attaching first and second pairs of elongate braces and said tibial plate to the exterior side of the flexible sheet after the sheet has been wrapped around the wearer's calf leg member; and g. a plurality of strong straps which are selectively attached to said braces, and adapted to encompass respective said braces, load bearing uprights, rear stays and tibial plate and which are adapted to be wrapped circumferentially around the wearer's calf member; said straps having connection means so they can be placed in tension around the wearer's calf leg member and secure to said braces, said load bearing uprights to hold in place said braces, rear stays, plate for providing substantial structural support without the necessity of a totally encompassing calf cast.

14. The tibial fracture walking brace module of the universal leg brace system of claim 13 wherein said load bearing uprights are hingedly connected with said shoe inserts so as to allow a pivotal action between said shoe insert and the upright portion of said load bearing uprights which are connected with said braces on either side of said calf of the wearer.

15. A method of affixing a universal leg brace system to a person's leg in order to control the degree of motion which can be permitted by the person's knee and also afford longitudinal structural support, comprising:

a. initially wrapping first and second flexible sheets of cushioned material around the person's leg members of the leg to be controlled, with one of the flexible sheets circumferentially enveloping most of the person's calf and the second flexible sheet circumferentially enveloping most of the person's thigh and securing said first and second sheets so they are at least temporarily held in place around their respective leg members;

b. subsequently positioning and then selectively attaching first and second pairs of elongated braces to the exterior sides of respective ones of the first and second flexible sheets after said sheets have been wrapped their associated leg members, and positioning said elongate braces such that hinges are properly located adjacent the person's knee on either side thereof;

c. connecting rear stays and front tibial and femoral plates with, respectively, the femoral and tibial leg members so as to provide significant longitudinal structural support; and d. wrapping a plaurality of straps circumferentially around the flexible sheets on the person's leg members, around the respective first and second pairs of braces, around the respective rear stays and around the respective plates; and placing the straps in tension so as to closely envelop the leg members and their associated elongate braces, stays, and plates for providing significant longitudinal structural support without the requirement of a fully enclosing leg cast.

16. The universal leg brace system of claim 1 wherein there are provided a load bearing brim that is adapted to be set into said brace system longitudinally on top of and above said stays and said femoral plate; an ankle cuff that is adapted to be emplaced about said ankle; and a shoe insert having load bearing uprights pivotally connected therewith; said load bearing uprights being adapted for being connected with said bottom elongate braces.

17. A femoral fracture walking brace system for providing longitudinal support for a wearer, comprising:

a. a shoe insert with load bearing uprights connected therewith; said load bearing uprights being adapted to be connected an other of first and second flexible sheets of b;

b. first and second flexible sheets of cushioned material, one of which being adapted for snugly wrapping around the wearer's thigh and the other being adapted for snugly wrapping around the wearer's calf, the width of each sheet being sufficient to circumferentially envelop at least most of its associated leg member, the length of each sheet being sufficient to encompass more than half the length of its respective leg member; said flexible sheets being selectively removeable and replaceable around the wearer's leg member;

c. first and second pairs of elongate braces, each of said braces being relatively stiff so as to resist both torsion and bending loads, said first pair of elongate braces being adapted to lie on opposite sides of the wearer's thigh and the second pair of elongate braces being adapted to lie on opposite sides of the wearer's calf;

d. at least first and second pairs of rear stays adapted for being connected respectively with said first and second flexible sheets for providing posterior structural support in the longitudinal direction; said first pair of rear stays being adapted to provide posterior structural support in the longitudinal direction along the posterior of the thigh; said second pair of rear stays being adapted to provide posterior structural support in the longitudinal direction along the posterior of the calf;

e. means for connecting said first and second pairs of rear stays with said first and second flexible strips;

f. tibial plate adapted for being connected respectively with said other flexible sheet around the wearer's calf for providing anterior structural support in the longitudinal direction; said tibial plate being adapted to provide anterior structural support in the longitudinal direction along the anterior portion of the calf;

g. means for adjustably positioning and selectively attaching said first and second pairs of elongate braces to said flexible sheets and said tibial plate to the exterior sides of said other sheet after said sheet has been wrapped around the wearer's calf leg member, said braces having central ends which are near one another when respective sheets are wrapped around their respective associated leg members and the braces are attached to the respective sheets;

h. hinge means attahced to respective central ends of said braces and adapted to lie on each side of the wearer's knee; said hinge means being effective for controlling the angle that is formed by the two braces on a given side of the wearer's leg;

i. a plurality of strong straps which are selectively attached to said braces and encompass respective said braces, rear stays and plates and which are adapted to be wrapped circumferentially around the wearer's respective leg members; said straps having connection means so that they can be placed in tension around the wearer's leg and secured to said braces and hold in place said braces, rear stays and plates for providing substantial structural support without the necessity of a totally encompassing leg cast;

j. a femoral plate adapted for being connected with said one of said flexible sheets and for providing anterior structural support in the longitudinal direction along the anterior portion of the thigh of the wearer; said femoral plate being adapted to be encompassed by said straps about said thigh of a wearer; and k. means for at least temporarily connecting said femoral plate with said one of said flexible sheets snugly wrapped around the wearer's thigh; said means for attaching said femoral plate being means for adjustably positioning and selectively attaching said femoral plate prior to being encompassed by said strong straps.

18. The tibial fracture walking brace of claim 17 wherein said load bearing uprights are hingedly connected with said shoe inserts so as to allow pivotal action between said shoe insert and the upright portion of said load bearing uprights which are connected with said flexible sheet and, hence, said braces on either side of said calf of the person; and wherein a load bearing brim is provided and set into said one of said flexible sheets so as to be supported by said femoral plate once said strong straps have been tightened therearound.

* * * * *